US011974778B1

United States Patent
Jung et al.

(10) Patent No.: US 11,974,778 B1
(45) Date of Patent: May 7, 2024

(54) SYSTEMS AND METHODS FOR IMPLANTING LONGITUDINAL INTRAFASCICULAR ELECTRODES

(71) Applicants: Ranu Jung, Miami, FL (US); Anil Thota, Miami, FL (US)

(72) Inventors: Ranu Jung, Miami, FL (US); Anil Thota, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 18/479,869

(22) Filed: Oct. 3, 2023

Related U.S. Application Data (60) Provisional application No. 63/498,442, filed on Apr. 26, 2023.

(51) Int. Cl.
- *A61B 17/34* (2006.01)
- *A61B 17/00* (2006.01)
- *A61B 17/28* (2006.01)

(52) U.S. Cl.
CPC .......... *A61B 17/3468* (2013.01); *A61B 17/28* (2013.01); *A61B 2017/00743* (2013.01)

(58) Field of Classification Search
CPC ............... A61B 17/3468; A61B 17/28; A61B 2017/00743; A61B 17/1128; A61B 50/20; A61N 1/0551; A61N 1/0556; A61N 1/0558; A61N 2001/058; A61M 25/02; A61M 2025/024; A61M 5/1418; A61F 2/0811; A61F 8/2002–0894
See application file for complete search history.

(56) References Cited

U.S. PATENT DOCUMENTS

| | | | |
|---|---|---|---|
| 7,460,913 B2 | 12/2008 | Kuzma et al. | |
| 10,549,099 B2 | 2/2020 | Kluger et al. | |
| 10,624,548 B2 | 4/2020 | Keisler | |
| 11,331,026 B2 | 5/2022 | Durand et al. | |
| 2007/0215759 A1* | 9/2007 | Heegaard | A61M 5/1418 248/90 |
| 2010/0268055 A1 | 10/2010 | Jung et al. | |

(Continued)

OTHER PUBLICATIONS

Daniel W. Tan et al., A neural interface provides long-term stable natural touch perception, U.S. Department of Veterans Affairs, Sci Transl Med. Oct. 8, 2014; 6(257): 257ra138; 25 pages.

(Continued)

*Primary Examiner* — Darwin P Erezo
*Assistant Examiner* — Brigid K Byrd
(74) *Attorney, Agent, or Firm* — Saliwanchik, Lloyd & Eisenschenk (57) ABSTRACT

Systems, devices, and methods for implanting target-specific multiple intrafascicular electrodes in peripheral nerves are provided to facilitate an implantation process that can reduce the difficulty of the implanting procedure and the time taken to implement the procedure. A longitudinal intrafascicular electrode implantation facilitator (LIFT) and a method for utilization of the LIFT for intrafascicular electrode implantation are provided. The LIFT can flatten the nerve to increase access to the number of fascicles available for implantation and supports the nerve during electrode implantation.

19 Claims, 2 Drawing Sheets

(56) References Cited

U.S. PATENT DOCUMENTS

| | | | |
|---|---|---|---|
| 2011/0218498 A1* | 9/2011 | Bierman | A61M 5/1418 |
| | | | 604/174 |
| 2015/0141786 A1 | 5/2015 | Durand et al. | |
| 2015/0335882 A1 | 11/2015 | Gross et al. | |
| 2017/0182312 A1 | 6/2017 | Durand et al. | |
| 2017/0333698 A1 | 11/2017 | Gerber et al. | |
| 2018/0264255 A1 | 9/2018 | Durand et al. | |
| 2019/0217083 A1 | 7/2019 | Raspopovic et al. | |
| 2020/0001003 A1* | 1/2020 | Amir | C09J 7/30 |
| 2023/0355865 A1* | 11/2023 | Larkin | A61M 5/1418 |

OTHER PUBLICATIONS

Hamid Charkhkar et al., High-density peripheral nerve cuffs restore natural sensation to individuals with lower-limb amputations, Journal of Neural Engineering 15 (2018) 056002, 14 pages.

* cited by examiner

SYSTEMS AND METHODS FOR IMPLANTING LONGITUDINAL INTRAFASCICULAR ELECTRODES

CROSS-REFERENCE TO RELATED APPLICATION

This application claims the benefit of U.S. Provisional Application Ser. No. 63/498,442, filed Apr. 26, 2023, the disclosure of which is hereby incorporated by reference in its entirety, including all figures, tables, and drawings.

GOVERNMENT SUPPORT

This invention was made with government support under EB027584 and EB023261 awarded by the National Institutes of Health. The government has certain rights in the invention.

BACKGROUND

In bioelectronic medicine and peripheral neuromodulation therapy applications, electrical stimulation of nerves is used to restore functionality lost due to disease or trauma. Peripheral neural interfaces (neural electrodes) are often used to deliver electrical stimulation or electrical charge to the nerve tissue for eliciting the desired neurological function/outcome. Of the available neural electrode types and configurations, intrafascicular electrodes can interface with a distinct group of nerve fibers that when stimulated elicit a distinct function.

BRIEF SUMMARY

Embodiments of the subject invention provide novel and advantageous systems, devices, and methods for implanting target-specific multiple intrafascicular electrodes in peripheral nerves to facilitate an implantation process that can reduce the difficulty of the implanting procedure and the time taken to implement the procedure. A longitudinal intrafascicular electrode (LIFE) implantation facilitator (LIFT) and a method for utilization of the LIFT for intrafascicular electrode implantation are provided. The LIFT can flatten the nerve to increase access to the number of fascicles available for implantation and supports the nerve during electrode implantation. The intrafascicular electrode implantation method streamlines the implantation procedure. The systems and methods can improve the efficiency of delivery and effectiveness of the use of existing intrafascicular electrodes by enhancing the implantation procedure. The systems and methods are efficient in reducing the complexity of the intrafascicular electrode implantation procedure and in reducing the time taken to implant multiple intrafascicular electrodes, as well as effectively increasing the intrafascicular electrode's inherent selectivity properties. The selectivity is enhanced by providing a way to increase access to the number of fascicles in the nerve during intrafascicular electrode implantation. By using multiple intrafascicular electrodes within a fascicle, further selectivity can be achieved by increasing the set of nerve fibers that are accessible within a fascicle by each intrafascicular electrode.

In an embodiment, a device for implanting at least one target-specific intrafascicular electrode in at least one peripheral nerve can comprise: a main body; a flat platform on an upper portion of the main body; a ledge extending upwards from the flat platform; a first channel formed in the main body and extending from the flat platform to a bottom of the main body; a first arm extending outward from the bottom of the main body and having an L shape such that a first nerve shaping slot is formed between the first arm and the main body; and a stabilizing slot formed in the bottom of the main body. The first arm can comprise a lateral arm portion extending laterally away from the bottom of the main body and a vertical arm portion extending upwards from the lateral arm portion towards the ledge. The stabilizing slot can have a width that is smaller than that of the ledge. An upper surface of the ledge can have a width that is smaller than that of an upper surface of the flat platform. The device can further comprise a second channel formed in the main body opposite from the first channel and extending from the flat platform to a bottom of the main body. The device can further comprise a second arm extending outward from the bottom of the main body, opposite from the first arm, and having an L shape such that a second nerve shaping slot is formed between the second arm and the main body. The first channel can be open to the first nerve shaping slot and/or the second channel can be open to the second nerve shaping slot. The ledge can comprise at least one slot configured to be gripped by a stabilizing tool (e.g., forceps) during implantation of the at least one target-specific intrafascicular electrode.

In another embodiment, a method for implanting at least one target-specific intrafascicular electrode in at least one peripheral nerve can comprise: providing a device as described herein; passing a first vessel loop through the stabilizing slot; disposing the device proximal to the at least one peripheral nerve; slipping the at least one peripheral nerve on the flat platform and into the first channel; sliding a second vessel loop or a first custom silicone insert into the first reshaping slot; and implanting the at least one target-specific intrafascicular electrode by gripping the ledge with a stabilizing tool and introducing the at least one target-specific intrafascicular electrode with an introducer tool. The sliding of the second vessel loop or the first custom silicone insert into the first reshaping slot can be performed using a forceps. The stabilizing tool can be, for example, a first forceps, and the introducer tool can be, for example, a second forceps (which can be different from the first forceps). The forceps used for sliding the vessel loop or custom silicone insert into the reshaping slot can be the same as or different from the first forceps and can be the same as or different from the second forceps. The method can further comprise sliding a third vessel loop or a second custom silicone insert into the second reshaping slot (e.g., using a forceps, which can be the same as or different from any forceps previously mentioned in this paragraph). The ledge can comprise at least one slot configured to be gripped by the stabilizing tool, and during the implanting of the at least one target-specific intrafascicular electrode, the at least one slot of the ledge can be gripped by the stabilizing tool.

DETAILED DESCRIPTION

Intrafascicular electrodes are the preferred choice, from among available neural electrode types and configurations, due to their ability to interface with a distinct group of nerve fibers that when stimulated elicit a distinct function. Neural electrodes that are highly flexible and small in diameter (e.g., microwires, nanowires) are highly desirable in advanced neuromodulation applications. Implanting these highly flexible and thin electrodes in the nerve, a soft and compliant tissue, is especially difficult and time-consuming for surgeons not routinely performing peripheral nerve surgery. Embodiments of the subject invention provide novel and advantageous systems, devices, and methods for implanting target-specific multiple intrafascicular electrodes in peripheral nerves to facilitate an implantation process that can reduce the difficulty of the implanting procedure and the time taken to implement the procedure. A longitudinal intrafascicular electrode (LIFE) implantation facilitator (LIFT) and a method for utilization of the LIFT for intrafascicular electrode implantation are provided. The LIFT can flatten the nerve to increase access to the number of fascicles available for implantation and supports the nerve during electrode implantation. The intrafascicular electrode implantation method streamlines the implantation procedure. The systems and methods can improve the efficiency of delivery and effectiveness of the use of existing intrafascicular electrodes by enhancing the implantation procedure. The systems and methods are efficient in reducing the complexity of the intrafascicular electrode implantation procedure and in reducing the time taken to implant multiple intrafascicular electrodes, as well as effectively increasing the intrafascicular electrode's inherent selectivity properties. The selectivity is enhanced by providing a way to increase access to the number of fascicles in the nerve during intrafascicular electrode implantation. By using multiple intrafascicular electrodes within a fascicle, further selectivity can be achieved by increasing the set of nerve fibers that are accessible within a fascicle by each intrafascicular electrode. Though reference is made to intrafascicular electrodes throughout this description, the LIFT can be used to implant other microwire-based intraneural electrodes (not just intrafascicular electrodes).

Advantages of the LIFT of embodiments of the subject invention include: 1) increasing selectivity by flattening the nerve to increase access to the number of fascicles available for implanting by distributing the fascicles along the axis of flattening; 2) reducing the invasiveness of the implantation procedure by avoiding extensive epineurial dissection to identify the fascicles; 3) reducing the complexity of the implantation process by stabilizing the nerve; 4) reducing the time to implant multiple electrodes; and 5) reducing possibility of trauma to the nerve during the electrode implantation process. Advantages of the intrafascicular electrode implantation methods of embodiments of the subject invention include: 1) streamlining the intrafascicular electrode implantation process; and 2) requiring less training in the intrafascicular electrode implantation process.

The two primary functions of the LIFT are as: 1) a nerve supporter to support the nerve during the implantation of multiple intraneural electrodes; and 2) a nerve shaper to reshape the nerve from circular to elongated ellipse to distribute the available fascicles along the major axis of the elongated ellipse. Three-dimensional (3D) models of the LIFT were developed using a Computer Aided Design software platform (Dassault Systèmes SolidWorks Corporation, MA, USA).

Figure 1:
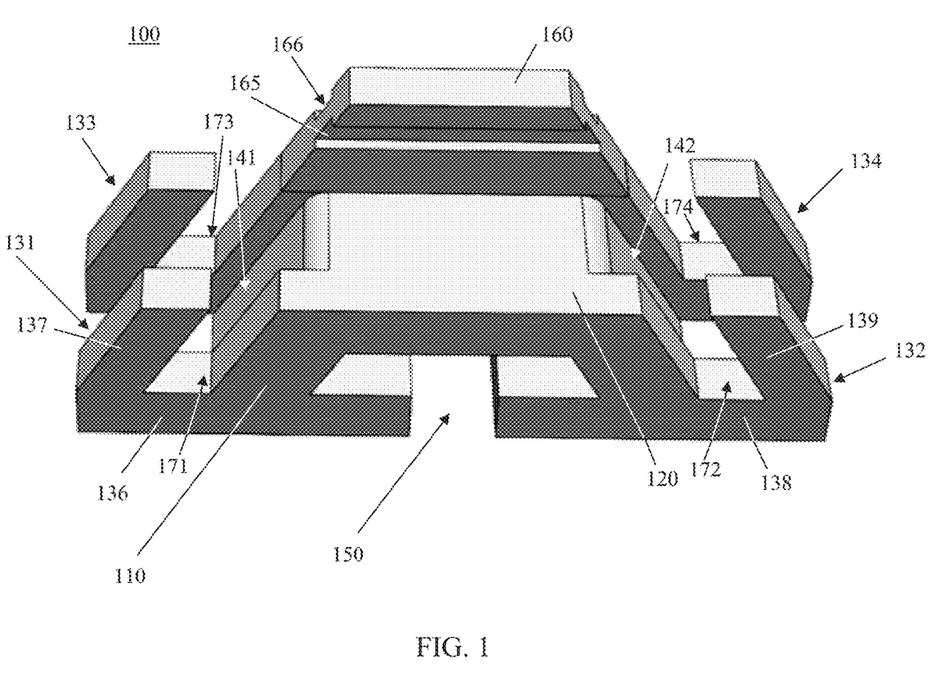
FIG. 1 shows a view of a longitudinal intrafascicular electrode implantation facilitator (LIFT), according to an embodiment of the subject invention.

FIG. 1 shows a schematic view of a LIFT, according to an embodiment of the subject invention. Referring to FIG. 1, a device 100 for implanting at least one target-specific intrafascicular electrode in at least one peripheral nerve can comprise: a main body 110; a flat platform 120 on an upper portion of the main body 110; a ledge 160 extending upwards from the flat platform 120 in a vertical direction perpendicular to the flat platform 120; a first channel 141 formed along a first side surface of the main body 110 and extending downwardly from the flat platform 120 to a bottommost surface of the main body 110; a second channel 142 formed along a second side surface of the main body 110 opposite from the first surface and extending downwardly from the flat platform 120 to the bottommost surface of the main body 110; a first arm 131 comprising a first lateral arm portion 136 extending away, in a first lateral direction parallel to the flat platform 120, from the bottommost surface of the main body 110 and a first vertical arm 137 portion extending upwards from the first lateral arm portion 136, the first vertical arm portion 137 extending towards the flat platform 120, and the first arm 131 having an L shape such that a first nerve shaping slot 171 is formed between the first arm 131 and the main body 110; a second arm 132 comprising a second lateral arm portion 138 extending away, in a second lateral direction opposite to the first lateral direction, from the bottommost surface of the main body 110 and a second vertical arm portion 139 extending upwards from the second lateral arm portion 138, the second vertical arm portion 139 extending towards the flat platform 120, and the second arm 132 having an L shape such that a second nerve shaping slot 172 is formed between the second arm 132 and the main body 110; and a stabilizing slot 150 that is a gap formed through an entirety of the bottommost surface of the main body 110 in the first and second lateral directions. The ledge 160 can comprise a first slot 165 and/or a second slot 166 that are configured to be gripped by a stabilizing tool during implantation of the at least on target-specific intrafascicular electrode. The first slot 165 can be a first indentation in the ledge 160 in a third lateral direction parallel to the flat platform 120 and perpendicular to the first and second lateral directions, and the second slot 166 can be indentation in the ledge 160 in a fourth lateral direction opposite to the third lateral direction. The device 100 can further comprise: a third arm 133 configured similarly to the first arm 131 and having an L shape such that a third nerve shaping slot 173 is formed between the third arm 133 and the main body 110; and/or a fourth arm 134 configured similarly to the second arm 131 and having an L shape such that a fourth nerve shaping slot 174 is formed between the fourth arm 134 and the main body 110. The nerve supporter's design features include the ledge 160, the flat platform 120, and the stabilizing slot 150. The nerve shaper's design features include the channels 141, 142 and the nerve shaping slots 171, 172, 173, 174, (which can also be referred to as reshaping slots).

In order to stabilize the LIFT and the nerve during the electrode implantation, one or more vessel loop (e.g., commercially available vessel loops) can be passed through the stabilizer slot 1SS. The platform 120 provides a uniform surface for the nerve to rest. One or more vessel loop (e.g., commercially available vessel loops) and/or one or more insert (e.g., silicone inserts such as custom silicone inserts) can be slid through the reshaping slots 171, 172, 173, 174 to secure the nerve in the channel(s) 141 and/or 142. The channel(s) 141 and/or 142 can reshape the nerve by applying small forces between the vessel loop placed in the reshaping slots and the bed of the channel. The ledge 160 with slots 165, 166 for microneedle holders or fine tweezers provides a stable and non-slip grip to further stabilize and manipulate the angle of the LIFT during the implantation of electrodes into the fascicles.

Figure 2:
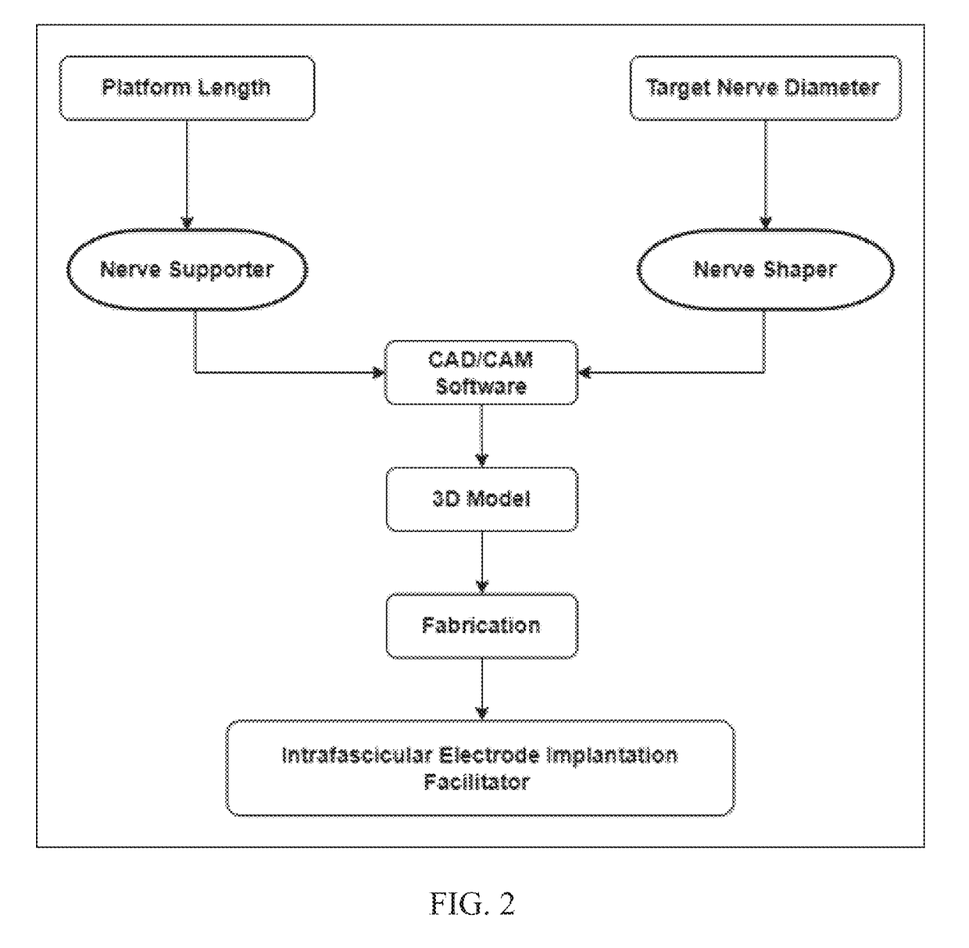
FIG. 2 shows a flowchart of a method of fabricating a LIFT, according to an embodiment of the subject invention.

The LIFT can be customized by varying the design parameters to fabricate LIFTs for implanting electrodes in nerves of different diameters. The platform length can be customized to accommodate different types of introducers and their lengths. The channel width and height can be customized to the degree of the required reshaping of the nerve. The channel's width and height can be pre-defined for a given nerve diameter to prevent potential nerve trauma. The pre-defined channel's width and height ensure that the cross-sectional area of the channel will always be greater than the cross-sectional area of the nerve, and the minimum height of the channel will always be greater than the largest fascicle diameter in the nerve. FIG. 2 shows a workflow for the fabrication of the LIFT, according to an embodiment of the subject invention, for modeling a custom device tailored to any nerve with nerve diameters above 1 millimeter (mm). The introducer length will determine the length of the platform. The target nerve diameter input will determine the channel's width and height for the nerve shaper function. Workflows can be used for modeling LIFTs tailored to a range of nerve diameter sizes encompassing small (1 mm to 5 mm), medium (5 mm to 10 mm), or large (10 mm to 20 mm) nerves.

LIFTs can be fabricated with, e.g., a 3D printer (e.g., a (commercially available) 3D fused deposition modeling printer) and can be used for preclinical animal testing. The units can be fabricated for deployable human use with Formlabs (Formlabs Inc, MA, USA) 3D printer and their biocompatible resin at FDA registered contract manufacturer. The LIFTs can also be fabricated using computerized numerical control (CNC) machines with various materials of choice for chosen applications.

The LIFT streamlines the intrafascicular electrode implantation process to reduce the complexity of the implantation. A modified version of one or more distributed intrafascicular multi-electrode (DIME) leads (e.g., three DIME leads) with each DIME lead having a plurality of LIFEs (e.g., five LIFEs) can be used. In the embodiment described here and validated in animal experiments, multiple individual LIFEs are used. Individual LIFEs can be fabricated as described in Thota et al. (A system and method to interface with multiple groups of axons in several fascicles of peripheral nerves, Journal of neuroscience methods, 244: 78-84, 2015, which is hereby incorporated by reference herein in its entirety).

An individual LIFE can be fabricated using, e.g., a highly flexible wire (e.g., platinum/iridium (Pt/Ir) (90%/10%) wire), a tungsten needle, and a stainless-steel metal plate. The wire with custom insulation is approximately 25 micrometers (μm) in diameter and 25 centimeters (cm) long. Approximately, a 1 mm area of the wire was de-insulated. The de-insulated portion of the wire forms a single contact LIFE. A tungsten needle, which acts as an introducer, is utilized to thread the LIFE into a fascicle in a nerve. Tungsten needles were fabricated using a pre-cut 2.5 cm, 75 μm tungsten rod. Tungsten rods were electro-sharpened on one end with 1 molar (1 M) sodium hydroxide using a custom-modified metal electrode etcher. The other end of the tungsten needle was ground with a dermal tool to create a saddle. The saddle portion of the needle was welded with a micro-welder to one end of the LIFE wire. The other end of the wire is welded to a small metal plate (approximately 2 mm×3 mm) for connecting to a neurostimulator.

Before using the LIFT, the nerve to be implanted is isolated from the surrounding connective tissue. The length of the isolated nerve for the example design illustrated here, was approximately 2.5 cm or longer. The facilitator can be designed to be smaller to access shorter nerve lengths. The diameter of the introducer (tungsten needle) limits the diameter of the nerve that can be implanted. Finer diameter introducers with sufficient rigidity, e.g., made from carbon fibers, could be utilized. Silicone vessel loops, or the surgeons' preferred method, can be utilized to manipulate the nerve for placement into the facilitator. The implantation steps are as follows:

Step 1: Pass the vessel loop through the vessel loop slot and place the device next to the nerve.

Step 2: Slip the nerve onto the device's platform and into the channel.

Step 3: Slide vessel loops or custom silicone inserts into the reshaping slots using a forceps.

Step 4: Implant the intrafascicular electrode by holding the ledge with a forceps and holding the electrode introducer with another forceps. Implant as many intrafascicular electrodes as needed.

The human peripheral nervous system (PNS) facilitates communication between the organs and glands in the body and the central nervous system (CNS). Bidirectional communications include the PNS relaying motor commands from the CNS to the voluntary muscles for the movement of limbs and sending sensory information, such as touch and pressure from the body's sensory organs to the CNS. This forms the somatic nervous system (SNS) component of the PNS. Besides, the PNS communicates CNS signals that assert involuntary control of bodily functions such as blood pressure, breathing, gut motility, urination, vision, and sweating by controlling several other body organs and glands, such as the heart, airways, stomach, bladder, pupils, and saliva. This forms the autonomic nervous system (ANS) component of the PNS. Pain is also linked with the autonomic nervous system.

Communication between the PNS and the CNS gets disrupted when degeneration, damage, or severing of nerve fibers and nerves occurs under certain disease or nerve trauma conditions. Disrupted communication leads to the loss of sensory, motor, autonomic, or a combination of one or more functions. Peripheral nerve fiber activation, using techniques such as electrical stimulation, is being utilized to re-establish communication of the CNS with the PNS. Such peripheral neuromodulation has been used to restore lost sensory functions in the extremities of individuals with lower and upper limb amputations, control neuropathic pain, relieve urinary bladder incontinence, and many other debilitating disease/trauma conditions.

Since the first description in the seventeenth century of the utilization of neural stimulation using peripheral neural interfaces (PNI) to elicit function, multiple researchers have used multiple types of peripheral nerve electrode interfaces to establish connectivity between the electrode and peripheral neural tissue to achieve the requisite neuromodulation or to record the activity of nerve fibers. Mammalian peripheral nerves include one or more nerve fascicles enveloped in epineurial tissue. An oligofascicular nerve can include 2-10 fascicles and polyfascicular nerves contain more than 10 fascicles. Each fascicle is comprised of groups of individual myelinated and/or unmyelinated nerve fibers wrapped in perineurial tissue. The most used PNI electrodes are nerve cuff electrodes. Cuff electrodes are wrapped around the nerve and have been used for over three decades. Injectrodes, that can be placed adjacent to the nerve, are alternatives to cuff electrodes that have been recently developed. To achieve close contact with nerve fibers, however, intraneural electrodes, and in particular intrafascicular electrodes have to be used.

The selectivity of an electrode is defined as the ability to interface with a distinct group of nerve fibers. Because the extensively used cuff electrodes are wrapped around the nerve and the injectrode is adjacent to the nerve, they are both farther from the nerve fibers inside the fascicles and hence typically have lower selectivity. Selectivity can be increased by placing the electrodes near the target nerve fibers. Thus, an intrafascicular electrode that penetrates nerve fascicles can interface directly with the target nerve fibers and hence promises higher selectivity. The highly selective electrode can be used in neuromodulation approaches to directly influence the activity of distinct groups of nerve fibers surrounding the electrode.

Neural electrodes designed to have high selectivity and specificity, such as intrafascicular electrodes, that can be utilized to achieve optimal therapeutic outcomes, may be especially desirable for use in an emerging neuromodulation research field, bioelectronic medicine. Bioelectronic medicine promises to improve and restore health without the debilitating side effects of systemically administered drugs by modulating neural communication between the brain and the end organs affected by diseases. Currently, PNIs, primarily cuff electrodes, are being used to stimulate nerves for treating diabetes, inflammation, rheumatoid arthritis, and many other disorders or disease conditions.

For achieving ideal goals for bioelectronic medicine applications, that would benefit from reduced off-target activation of nerve fibers, inevitable with cuff and injectrode type PNIs, the following PNI characteristics should be considered: 1) the PNI permits accessing a small group of fibers within each nerve fascicle; 2) the PNI offers reliable recording or stimulation of the fibers over the PNI's lifespan; and 3) the PNI does not harm the host nerve. Intrafascicular electrodes, offer these characteristics. Although more invasive to the nerve than nerve cuff electrodes, they offer more selectivity in achieving the intended nerve stimulation response and hence are ideal neural electrodes for bioelectronic medicine applications. In either completed or ongoing human research/clinical studies to interface with the somatic nervous system, three types of intrafascicular electrodes have been utilized: 1) Utah Slanted Electrode Array (USEA); 2) Transverse Intrafascicular Multichannel Electrode (TIME); and 3) LIFEs.

LIFEs offer high selectivity as well as good mechanical compatibility with the peripheral nerve into which they are implanted because each electrode is fabricated with a highly flexible insulated microwire. A tungsten needle (or other introducer) is attached at one end to insert the wire into the fascicle so that the active contact area for delivering electrical charge lies longitudinally within the fascicle parallel to the nerve fibers. The needle (or introducer) is discarded after the implantation. The longitudinal placement of the microwire parallel to the nerve fibers is also compatible with the inevitable stretching of peripheral nerves as the body moves. LIFEs have been implanted in human participants in research studies. For increasing selectivity, multiple LIFEs can be implanted in one or more fascicle within a nerve. To permit management of these fine microwires, that could easily get entangled and damaged during the surgical implantation procedure, we have previously developed a DIME lead including multiple LIFEs packaged in a single lead, and a multi-lead multi-electrode (MLME) system to facilitate implanting multiple DIMEs in multiple nerves. A slightly modified version of the DIME and MLME system is being utilized in an ongoing device feasibility Clinical Trial, NCT03432325. In this clinical trial, intrafascicular electrodes are implanted in nerve fascicles in the upper arm in individuals with amputation below the elbow with the intention of providing sensory feedback to the individual from advanced sensorized prosthetic hands.

The MLME system permits implantation of multiple LIFEs to access multiple nerves and fascicles while reducing risks of fine wire breakage and entanglement. However, the surgical implantation approach for maximizing selectivity and specificity by targeting multiple fascicles offers challenges, especially to surgeons not accustomed to routine peripheral nerve surgery. Some fascicles in a polyfascicular nerve are not easily accessible for electrode implantation because the nerve is oval, and the nerve can easily buckle during implantation because the nerve is a compliant structure. Implantation of multiple electrodes further increases implantation complexity and time to implant. Hence, we have developed and validated a system and method for implanting target-specific multiple intrafascicular electrodes to solve the above challenges.

Embodiments of the subject invention aid in implantation of the DIME and any other configuration of LIFEs, as well as reduce the invasiveness of the intrafascicular electrode implantation procedure. The latter is accomplished by: avoiding extensive epineurial dissection to identify the fascicles; reducing the complexity of the implantation process by stabilizing the nerve; reducing the time for implantation of multiple electrodes; and reducing nerve trauma during the electrode implantation process. Embodiments of the subject invention also increase selectivity of intrafascicular electrodes, streamlines the intrafascicular electrode implantation process, manages surgical space by isolating the nerve from surroundings during electrode implantation, and reduces need for surgical training and specialization of surgeons thereby making nerve implants for bioelectronic medicine available more widely and with lower costs.

When ranges are used herein, combinations and subcombinations of ranges (e.g., subranges within the disclosed range), as well as specific embodiments therein, are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Materials and Methods

In vivo testing of the facilitator was conducted on anesthetized rats (n=9; Male, Sprague Dawley, 430 (338-556) gms). The primary purpose of the acute non-survival in vivo testing was to show that the LIFEs implanted using the systems and methods of embodiments of the subject invention remain functional and allow desired on-target stimulation. Rats were anesthetized with isoflurane (1.5-2.5% in medical-grade oxygen) gas anesthesia. As per the IACUC guidelines, the well-being of rats was maintained by applying ophthalmic ointment to the eyes to prevent corneal desiccation, periodically administering saline subcutaneously to prevent dehydration, and placing the body on thermal pads to prevent hypothermia. Throughout the procedure, rodent body temperature was monitored by placing a temperature probe in the rectum, and physiological indicators (respiratory rate, heart rate, and SpO2) were monitored using a vital signs monitor (Smith Medical, Model: Surgivet® Advisor® Vital Sign Monitor, OH, USA). The level of anesthesia was periodically assessed with toe pinch, observation of eye blink, and the respiration rate.

The sciatic nerve was accessed by making a straight incision from the lateral aspect of the thigh to the ankle joint, followed by separating the biceps femoris and gluteus superficialis through minimal dissection techniques. The separated muscles were held using elastic stays and self-retaining retractors (Cooper Surgical, Model: Lone Star, CT, USA) to reach the sciatic nerve. The nerve was isolated by separating it from the surrounding connective tissue.

After the isolation of the sciatic nerve, vessel loops (Aspen Surgical, Model: Maxi, MI, USA) were placed around the isolated nerve to manipulate the nerve. Three to four LIFEs were implanted while viewing the nerve under a surgical microscope (Leica Microsystems, Model: M320, IL, USA) with >6.4 magnification. The electrode implantation process was performed according to embodiments of the subject invention as described herein. After implantation, the electrodes were secured to the epineurium proximally and distally with 8-0 non-absorbable sutures.

The functionality of the systems and methods of embodiments of the subject invention was shown by quantifying hindlimb muscle contractions on electrically stimulating the nerve fibers of the sciatic nerve with the LIFEs implanted with the systems and methods of embodiments of the subject invention. Stimulating nerve fibers in the peroneal fascicle of the nerve generate flexor muscle (Tibialis Anterior (TA)) contractions and elicit an ankle flexion response. Similarly, stimulating nerve fibers in the tibial fascicle of the nerve generates contractions in the extensor muscle group (Gastrocnemius (GM) and synergistic muscles) and elicits an ankle extension response. A computer-controlled neurostimulator (see also Kolbl et al., IC-Based Neuro-Stimulation Environment for Arbitrary Waveform Generation, Electronics (15): 1867, 2021; which is hereby incorporated by reference herein in its entirety) was attached to each of the LIFEs to stimulate the peroneal and tibial fascicles of the sciatic nerve. The impact of muscle contractions was quantified by measuring the change in ankle joint angle or the isometric force generated by the hindlimb. The rat's hindlimb was videotaped for offline analysis to obtain ankle joint angle data. In order to collect isometric force data, the rat's paw and the ankle joint were securely attached to a six-degree-of-freedom load cell (JR3, Inc., Woodland, CA, USA) using a custom 3D-printed shoe. A custom Python code was written to send the stimulation parameters (pulse width (PW) and pulse amplitude (PA)) to the computer-controlled neurostimulator.

Before collecting functional (joint angle and force) data, the stimulation space (combination of PW and PA) was determined by computing strength-duration (SD) curves. To compute the SD curve, the stimulation PWs varied from 10 μs to 300 μs in different trials distributed either linearly or logarithmically. For each PW, the PA values were gradually increased until the muscle twitch response (PWtw, PAtw) was observed and recorded. The twitch response was identified when a noticeable first twitch of the hindlimb was visually observed, or a change in force profile from the baseline was observed. An SD curve for each LIFE was plotted with PWtw on the x-axis and PAtw on the y-axis. The nerve excitability properties (rheobase and chronaxie) were derived from the plotted SD curve. The rheobase current is the minimum PA that initiates an action potential at a very long PW. The chronaxie time is the PW corresponding to twice the rheobase current. The initial stimulation parameter pair (PWth, PAth) for each LIFE was determined from the chronaxie time and rheobase current. The PWth was set as the chronaxie time value, and PAth was set as 2x rheobase current.

Example 1—Stimulation and Isometric Force Assessment

The force data were recorded in seven rats at a 30 kilohertz (kHz) sampling rate using a Scout neurorecording system (Ripple Neuro, Salt Lake City, UT, USA). The stimulation pulses from the neurostimulator were also recorded to synchronize the force data with the stimulation parameters.

Example 2—Recruitment Curves

Recruitment curves show the ability of the electrodes to activate nerve fibers as a function of injected charge (PW× PA). The recruitment curves were derived from the force data generated by isometric muscle contractions through electrical stimulation of nerve fibers in the sciatic nerve. For each LIFE, multiple stimulation pairs (PW and PA) were chosen from the SD curve such that the PA and PW values fall above the threshold charge delivery level to obtain a measurable functional outcome. All the stimulation pairs were randomized before sending the array of the stimulation parameters to the stimulator. A burst of five stimulation pulses, one for every second, was sent to activate the nerve fibers, and the burst repeated with a new set of parameters after 20 seconds.

Example 3—Ankle Joint Force Assessment

In two rats, the LIFEs (one from the tibial and one from the peroneal fascicle) were stimulated alternatively to generate forces that could produce cyclic movements similar to walking gait kinematics. In addition, to grade muscle contractions with a change in stimulation frequency, the electrodes were stimulated with PW set as PWth and PA as PAth, and the stimulation frequency varied between 10, 30, and 50 Hertz (Hz). Each electrode's stimulation sequence was set with a burst of stimulation ON for about 500 milliseconds (ms) at the desired frequency, followed by stimulation OFF for about 500 ms. This sequence was alternated between the electrodes in each fascicle for twenty cycles. The ON and OFF stimulation time was inconsistent because the timing process was software-controlled over USB communication instead of hardware control. In addition, to grade muscle contractions with a change in stimulation amplitude, the electrodes were stimulated with PW set as PWth, stimulation frequency was set at 50 Hz, and PA varied between 1.5× PAth, 2.0×PAth, and 2.5×PAth.

Example 4—Stimulation and Ankle Joint Angle Assessment

In two rats, the LIFEs (one from the tibial and one from the peroneal fascicle) were stimulated alternatively to produce cyclic movements similar to walking gait pattern. The bony processes of the metatarsal, ankle, and knee joints were highlighted by placing retroreflective markers for offline video data processing and analysis. The video data was collected at 30 frames per second using a single high-definition camera (Logitech, Model C922, Nijmegen, Netherlands). Using a tripod, the video camera was positioned approximately perpendicularly to the rat's hindlimb. The LIFEs in peroneal and tibial fascicles were stimulated with the PW set as PWth and PA as 1.5 times PAth. To grade muscle contractions with a change in stimulation frequency, the electrodes were stimulated with PW set as PWth and PA as 1.5×PAth, and the stimulation frequency varied among 30 Hz, 40 Hz, and 50 Hz. A 10 Hz stimulation frequency was not chosen because we observed from the force data that the muscle contractions were not fused below 30 Hz stimulation.

Example 5—Isometric Force Assessment

A suite of custom Matlab® routines, including modifications to application interface (API) routines provided by the neurorecording system manufacturer, was developed to extract, transform, process, and analyze the force data. In order to remove high-frequency noise, the raw data were low-pass filtered with a 4th-order Butterworth filter at 50 Hz. The filter was applied twice (once forward and then backward) to reduce the phase difference. The resultant force was calculated using the x-, y-, and z-axis components. In addition, the force data from recruitment curves were synchronized and averaged using the stimulation pulses across the five data segments. To derive recruitment curves, the maximum peak value of the resultant force for each stimulation pair was obtained and plotted.

Example 6—Ankle Joint Angle Assessment

The captured video data was imported into validated Kinovea (kinovea.org) kinematic analysis software (Zult et al., A low-cost 2-D video system can accurately and reliably assess adaptive gait kinematics in healthy and low vision subjects, Scientific Reports 9(1): 18385, 2019; which is hereby incorporated by reference herein in its entirety). The ankle angle was defined by three markers placed on the rat hindlimb. The markers in the video were digitized to obtain ankle angle data. The ankle data was exported to Matlab® to plot.

Both force and ankle joint angle assessments showed that the electrodes implanted using the systems and methods of embodiments of the subject invention produced expected and appropriate stimulus responses; hence, the electrodes were functional.

Example 7—Stimulation and Isometric Force Assessment

The peak force value increased with increasing PA for a given PW as well as for increasing PW for a given PA. This peak force value indicates that the stimulation using LIFEs could recruit more motor fibers as the stimulation charge (PW×PA) increases. At lower PA values, the recruitment curves form a typical "S" shape. The plateau at the lower portion (low charge) of the "S" shape indicates hardly any response due to the inability to recruit nerve fibers. The plateau at the top portion (high charge) of the "S" shape indicates that the response is plateaued because of recruiting all the available nerve fibers. In between the "S-shaped" region, the response increases monotonically as the charge increases, indicating that the increasing charge increases the number of nerve fibers recruited. The force generated by stimulating the peroneal fascicle was smaller than that generated by stimulating the tibial fascicle. This difference in the force indicates that the larger muscle (GM), by weight and volume, generated a higher force than the smaller muscle (TA).

The stimulation of electrodes in the peroneal fascicle primarily elicited ankle flexion (up (pull force)) and in the tibial fascicle primarily elicited ankle extension (down (push force)). The force transducer records reactionary force (equal and opposite) to the muscle contraction force. This shows that electrodes implanted with systems and methods of embodiments of the subject invention are highly selective. In addition, the force generated by both muscles increases with an increase in PA. A similar trend, an increase in force, was also observed with an increase in stimulation frequency. However, the contractions were not fused, seen as a series of muscle twitches for 10 Hz stimulation frequency. At 50 Hz stimulation, the muscle contractions were fused entirely.

Example 8—Stimulation and Ankle Joint Angle Assessment

The stimulating electrode in the peroneal fascicle produced ankle flexion (decrease in ankle angle; the foot moved towards the body), and the stimulating electrode in the tibial fascicle produced ankle extension (increase in ankle angle; the foot moved away from the body). Stimulation above 30 Hz produced fused contractions in a distinct direction (ankle flexion vs. ankle extension), and the ankle angle increased with the increased stimulation frequency.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A device for implanting at least one target-specific intrafascicular electrode in at least one peripheral nerve, the device comprising:
a main body;
a flat platform on an upper portion of the main body;
a ledge extending upwards from the flat platform in a vertical direction perpendicular to the flat platform;
a first channel formed along a first side surface of the main body and extending downwardly from the flat platform to a bottom most surface of the main body;
a second channel formed along a second side surface of the main body opposite fro the first side surface and extending downwardly from the flat platform to the bottommost of the main body;
a first arm comprising a first lateral arm portion extending away, in a first lateral direction parallel to the flat platform, from the bottommost surface of the main body and a first vertical arm portion extending upwards from the first lateral arm portion, the first vertical arm portion extending towards the flat platform, and the first arm having an L shape such that a first nerve shaping slot is formed between the first arm and the main body;
a second arm comprising a second lateral arm portion extending away, in a second lateral direction opposite to the first lateral direction, from the bottommost surface of the main body and a second vertical arm portion extending upwards from the second lateral arm portion, the second vertical arm portion extending towards the flat platform, and the second arm having an L shape such that a second nerve shaping slot is formed between the second arm and the main body; and
a stabilizing slot that is a gap formed through an entirety of the bottom most surface of the main body in the first and second lateral directions,
the stabilizing slot being disposed below the flat platform in the vertical direction,
the first channel facing the first lateral direction and being open to an outside in the first lateral direction, and
the second channel facing the second lateral direction and being open to the outside in the second lateral direction.

2. The device according to claim 1, the main body comprising a space, in the vertical direction, between the stabilizing slot and the flat platform.

3. The device according to claim 1, the stabilizing slot having a width, in the first and second lateral directions, that is smaller than that of the ledge, in the first and second lateral directions.

4. The device according to claim 1, an uppermost surface of the ledge having a width, in the first and second lateral directions, that is smaller than that of the flat platform, in the first and second lateral directions.

5. The device according to claim 1, the ledge extending upwards from an outermost edge of the flat platform.

6. The device according to claim 1, the ledge comprising a first slot and a second slot that are configured to be gripped by a stabilizing tool during implantation of the at least one target-specific intravesicular electrode,
the first slot being a first indentation in the ledge in a third lateral direction parallel to the flat platform and perpendicular to the first and second lateral directions,
the second slot being a second indentation in the ledge in a forth lateral direction opposite to the third lateral direction, and
the first slot and second slot both being disposed below, in the vertical direction, an uppermost surface of the ledge.

7. The device according to claim 1, the first channel being open to the first nerve shaping slot, and
the second channel being open to the second nerve shaping slot.

8. The device according to claim 1, the ledge comprising a slot configured to be gripped by a stabilizing tool during implantation of the at least one target-specific intrafascicular electrode,
the slot being an indentation in the ledge in a third lateral direction parallel to the flat platform and perpendicular to the first and second lateral directions, and
the slot being disposed below, in the vertical direction, an uppermost surface of the ledge.

9. A method for implanting at least one target-specific intrafascicular electrode in at least one peripheral nerve, the method comprising:
providing the device according to claim 1;
passing a first vessel loop through the stabilizing slot;
disposing the device proximal to the at least one peripheral nerve;
slipping the at least one peripheral nerve on the flat platform and into the first channel;
sliding a second vessel loop or a first custom silicone insert into the first nerve shaping slot; and
implanting the at least one target-specific intrafascicular electrode by gripping the ledge with a stabilizing tool and introducing the at least one target-specific intrafascicular electrode with an introducer tool.

10. The method according to claim 9, the sliding of the second vessel loop or the first custom silicone insert into the first nerve shaping slot being performed using a forceps.

11. The method according to claim 9, the stabilizing tool being a first forceps.

12. The method according to claim 11, the introducer tool being a second forceps different from the first forceps.

13. The method according to claim 9, the introducer tool being a forceps.

14. The method according to claim 9, further comprising sliding a third vessel loop or a second custom silicone insert into the second nerve shaping slot.

15. The method according to claim 9, the first channel being open to the first nerve shaping slot.

16. The method according to claim 9, the ledge comprising at least one slot configured to be gripped by the stabilizing tool, and
during the implanting of the at least one target-specific intrafascicular electrode, the at least one slot of the ledge is gripped by the stabilizing tool.

17. A device for implanting at least one target-specific intrafascicular electrode in at least one peripheral nerve, the device comprising:
a main body;
a flat platform on an upper portion of the main body;
a ledge extending upwards from an outermost edge of the flat platform in a vertical direction perpendicular to the flat platform;
a first channel formed along a first side surface of the main body and extending downwardly from the flat platform to a bottommost surface of the main body;
a second channel formed along a second surface of the main body opposite from the first side surface and extending downwardly from the flat platform to the bottommost surface of the main body;

a first arm comprising a first lateral arm portion extending away, in a first lateral direction parallel to the flat platform, from the bottommost surface of the main body and a first vertical arm portion extending upwards from the first lateral arm portion, the first vertical arm portion extending towards the flat platform, and the first arm having an L shape such that a first nerve shaping slot is formed between the first arm and the main body;

a second arm comprising a second lateral arm portion extending away, in a second lateral direction opposite to the first lateral direction, from the bottommost surface of the main body and a second vertical arm portion extending upwards from the second lateral arm portion, the second vertical arm portion extending towards the flat platform, and the second arm having an L shape such that a second nerve shaping slot is formed between the second arm and the main body;

a third arm comprising a third lateral arm portion extending away, in the first lateral direction, from the bottommost surface of the main body and a third vertical arm portion extending upwards from the third lateral arm portion, the third vertical arm portion extending towards the flat platform, and the third arm having an L shape such that a third nerve shaping slot is formed between the third arm and the main body;

a fourth arm comprising a fourth lateral arm portion extending away, in the second lateral direction, from the bottommost surface of the main body and a fourth vertical arm portion extending upwards from the third lateral arm portion, the fourth vertical arm portion extending towards the flat platform, and the fourth arm having an L shape such that a fourth nerve shaping slot is formed between the fourth arm and the main body;

a stabilizing slot that is a gap formed through an entirety of the bottommost surface of the main body in the first and second lateral directions, the stabilizing slot being disposed below the flat platform in the vertical direction, the first channel facing the first lateral direction and being open to an outside in the first lateral direction, the second channel facing the second lateral direction and being open to the outside in the second lateral direction, the main body comprising a space, in the vertical direction, between the stabilizing slot and the flat platform, the stabilizing slot having a width, in the first and second lateral directions, that is smaller than that of the ledge in the first and second lateral directions, an uppermost surface of the ledge having a width, in the first and second lateral directions, that is smaller than that of the flat platform in the first and second lateral directions, the first channel being open to the first nerve shaping slot and the third nerve shaping slot, the second channel being open to the second nerve shaping slot and the fourth nerve shaping slot, the ledge comprising a first slot and a second slot that are configured to be gripped by a stabilizing tool during implantation of the at least one target-specific intrafascicular electrode, the first slot being a first indentation in the ledge in a third lateral direction parallel to the flat platform and perpendicular to the first and second lateral directions, the second slot being a second indentation in the ledge in a forth lateral direction opposite to the third lateral direction, and the first slot and second slot being disposed below, in the vertical direction, the uppermost surface of the ledge.

18. A method for implanting at least one target-specific intrafascicular electrode in at least one peripheral nerve, the method comprising:

providing the device according to claim 17;

passing a first vessel loop through the stabilizing slot;

disposing the device proximal to the at least one peripheral nerve;

slipping the at least one peripheral nerve on the flat platform and into the first channel;

sliding a second vessel loop or a first custom silicone insert into the first nerve shaping slot;

sliding a third vessel loop or a second custom silicone insert into the second nerve shaping slot; and implanting the at least one target-specific intrafascicular electrode by gripping the ledge with a stabilizing tool and introducing the at least one target-specific intrafascicular electrode with an introducer tool.

19. The method according to claim 18, the sliding of the second vessel loop or the first custom silicone insert into the first nerve shaping slot being performed using a first forceps, the sliding of the third vessel loop or the second custom silicone insert into the second nerve shaping slot being performed using the first forceps, the stabilizing tool being a second forceps, the introducer tool being a third forceps different from the second forceps, the first forceps being the same as or different from each of the second forceps and the third forceps.

* * * * *